United States Patent [19]

Khachatoorian

[11] Patent Number: 5,895,627
[45] Date of Patent: Apr. 20, 1999

[54] SIMPLIFIED ETHYLENE OXIDE STERILIZATION TEST PACK

[75] Inventor: Armineh Khachatoorian, La Crescenta, Calif.

[73] Assignee: Minnesota Mining and Manufacturing Company, St. Paul, Minn.

[21] Appl. No.: 08/808,598

[22] Filed: Feb. 28, 1997

[51] Int. Cl.⁶ .................................................. G01N 21/09
[52] U.S. Cl. ............................ 422/58; 422/61; 422/86; 422/87; 422/294; 73/23.2; 436/1
[58] Field of Search ................................ 422/27, 34, 61, 422/58, 86, 87, 292, 294; 436/1; 73/23.2

[56] References Cited

U.S. PATENT DOCUMENTS

| | | | |
|---|---|---|---|
| 3,752,743 | 8/1973 | Henshilwood | 195/127 |
| 4,115,068 | 9/1978 | Joslyn | 422/56 |
| 4,138,216 | 2/1979 | Larsson et al. | 422/56 |
| 4,304,869 | 12/1981 | Dyke | 435/296 |
| 4,348,209 | 9/1982 | Murtaugh et al. | 422/61 |
| 4,461,837 | 7/1984 | Karla | 435/296 |
| 4,591,566 | 5/1986 | Smith | 435/291 |
| 4,594,223 | 6/1986 | Dyke et al. | 422/56 |
| 4,739,881 | 4/1988 | Bruso | 206/305 |
| 4,828,797 | 5/1989 | Zwarun et al. | 422/55 |
| 4,839,291 | 6/1989 | Welsh et al. | 435/296 |
| 4,863,867 | 9/1989 | Joyce et al. | 435/287 |
| 4,914,034 | 4/1990 | Welsh et al. | 435/296 |
| 5,167,923 | 12/1992 | Van Iperen | 422/58 |

FOREIGN PATENT DOCUMENTS 0 255 229 A2  6/1987  European Pat. Off. .
0 419 282 A1  9/1990  European Pat. Off. .

*Primary Examiner*—Lyle A. Alexander
*Attorney, Agent, or Firm*—Gary L. Griswold; Robert W. Sprague; Jeffrey J. Hohenshell

[57] ABSTRACT

A test pack for evaluating an ethylene oxide sterilization process, comprising an open ended fiber board tubular member, an end cap enclosing each end of said tubular member, said end caps defining a test chamber within the tubular member, one of said end caps having an opening to permit the egress of ethylene oxide into the test chamber. A fiber ball is inserted into the test chamber at a location remote from the end cap having the opening therein, and a chemical type sterilization indicator is placed within the test chamber.

9 Claims, 2 Drawing Sheets

SIMPLIFIED ETHYLENE OXIDE STERILIZATION TEST PACK

FIELD OF THE INVENTION

This invention relates to a test pack for an ethylene oxide sterilization process. In particular it relates to an ethylene oxide test pack utilizing a chemical sterilization indicator.

BACKGROUND OF THE INVENTION

U.S. Pat. No. 4,304,869, discloses an apparatus for rupturing a sealed frangible container. The frangible container is enclosed in an elongated tubular member having an annular space of decreasing dimension. The frangible container, e.g. a vial, contains a biological indicator for the sterilization process. The device is utilized to measure the effectiveness of steam or gas sterilization process. The tubular member is enclosed at each end. The device is fitted together by insertion of an end cap which can support the frangible container into a flanged section. Sterilant passes into the tubular member between the flanged portion and the cap which presents a tortuous path for the sterilant which may be steam or a gas.

U.S. Pat. No. 4,461,837, discloses a biological system for use in sterilization processes. A container is provided to enclose a frangible vial containing a biological indicator. The sterilant gas gains access to the indicator comprising spore strips by passing through the annulus formed by the outer dimension of the tubular container and a cap fitted at one end. The sterilant fluid communication between the exterior and interior of the container is described as taking place along a tortuous path because fluid traversing the path must negotiate at least two 90° turns in order to gain access to the interior of the container.

U.S. Pat. No. 4,914,034, discloses a disposable biological test pack for monitoring steam and ethylene oxide sterilization processes. The test pack comprises a fiberboard housing which includes two end sections and a midsection. Each end section includes an outer tube and a longer inner tube. The open end of the outer tubes abut the opposing ends of the midsection to define a seam or gap. The inner tube extends past the seam and telescopes into the midsection. The seam and the close tolerance between the inner tube and midsection provide a tortuous path for entry of the sterilant into the interior of the housing. The tortuous path has a moisture absorbent surfaced and is dimensioned to promote intimate contact between the sterilant and absorbent surface. A second path of entry is provided for ethylene oxide sterilization processes only. In the ethylene oxide process the ETO reaches the biological indicator via a second tortuous path, and to a lesser extent through the first tortuous path.

U.S. Pat. No. 4,591,566, discloses a biological indicator probe for steam sterilization systems. The probe comprises a rod of heat resistant material, i.e., polysulphone resin, having an end chamber (test probe element) closable by a rotatable sleeve. The test probe element is made of the same material as the rod. The test probe element is adapted to accept a test vial containing the biological indicator through closable windows. The test vial is exposed to the steam and high temperature of the autoclave through the windows.

U.S. Pat. No. 4,839,291, discloses a disposable biological indicator test pack for monitoring steam and ethylene oxide sterilization processes. The test pack includes a fiber board housing for a biological indicator comprising an outer tube and a shorter inner tube. The outer tube has upper and lower portions which define a seam or gap at their adjoining ends. The inner tube extends past the seam and telescopes into the upper and lower portions of the outer tube. The seam and the close tolerance between the inner tube and the outer tube prove a tortuous path for entry of sterilant into the interior of the housing. The tortuous path has a moisture absorbing surface and is dimensioned to promote intimate contact between the sterilant and the absorbent surface. A hole covered by an optionally removable tab is provided at the end of the upper portion of the outer tube for use in monitoring ethylene oxide sterilization processes. The vial containing the biological indicator is enclosed in ampule having a cap. The space between the cap and the outer ampule wall provides an additional tortuous path for entry of sterilant into the biological indicator.

European Patent Application No. 0 255 229 A2 discloses a steam sterilization test pack comprising a plastic tube having a steam sensitive sterilization card and a biological indicator therein. The tube has end caps both of which have centrally located apertures. The caps have an inside diameter slightly larger than the outside diameter of the tube. The spacing between the cap and tube provide a circuitous path for the entry of steam.

European Patent Application No. 0 419 282 A1 discloses a disposable test pack for steam or gas sterilization. The test pack comprises a container filled with porous packing material. The packing material challenges the penetration of the sterilant by providing a restricted pathway which acts to impede the flow of sterilant through the test pack. The test pack can contain either a biological or chemical indicator or both to detect the efficacy of the sterilization process.

Whether used for steam or ethylene oxide process monitoring, the devices of the prior art require a tortuous path, provided either by geometric design of the device or by packing, for the entry of sterilant into the test chamber. Generally the indicator is a biological indicator, though chemical indicators are disclosed.

The Association for the Advancement of Medical Instrumentation (AAMI) has developed a protocol for testing the ETO sterilization process which comprises the utilization of a large plastic syringe into which a biological indicator can be placed. The syringe has an elongated constricted element, integral with the syringe at one end in place of a needle, and a plunger at the end remote to the constricted element. After the indicator is placed into the syringe the plunger is put into place, thereby leaving only the elongated element as an entry way for the ETO. The device is wrapped in a large towel and placed into the sterilizer for the purpose of monitoring the sterilization process.

This procedure has been modified by replacing the towel by a fiber board cylinder which is dimensioned to fit snugly over the syringe body. The cylinder serves as a heat sink as well as absorbing ETO and moisture to delay the kill rate of the spores within the biological monitor, usually spore strips having specific resistant strains of microbes deposited thereon.

U.S. Pat. No. 4,138,216, discloses a chemical type ethylene oxide indicator. The device comprises a wick enclosed in an ethylene oxide (ETO) impervious envelope having the wick exposed at one end. The wick is impregnated with a magnesium halide which is reactive with ETO to form a base, the presence of which is detected by a pH sensitive dye incorporated into the wick.

In use the chemical indicator is enclosed in a pack of material which requires sterilization. The pack offers resistance to the entry of ethylene oxide. Hence the indicator will indicate the quality of the process to which the material to be sterilized is exposed. Examination of the chemical indicator requires opening the pack to view it, thereby exposing the sterilized contents to potentially septic conditions. It is of value to be able to monitor the effectiveness of the sterilization process without the need to open a sterilized package. Use of the chemical process monitor of the '216 patent without a pack results in erroneous results in that the device is designed to be utilized in a pack, and indicate sterilization after adequate exposure to ETO for the proper time under appropriate humidity conditions. What is needed is a method for utilizing the chemical process monitor without enclosing it in a pack of material requiring sterilization, thereby permitting ready access to the monitor in order to evaluate the efficacy of the sterilization process.

SUMMARY OF THE INVENTION

It has surprisingly been found that a suitable test pack for a chemical type ETO sterilization process integrator can be devised utilizing a fiber board tube. The test pack comprises a fiber board tube having end caps defining an interior chamber into which the chemical type indicator is disposed. One cap is perforated with an opening to permit the egress of ETO to the chamber. A ball of fibrous material is placed at the end of the chamber remote from the perforated cap.

DETAILED DESCRIPTION OF THE INVENTION

Figure 1A:
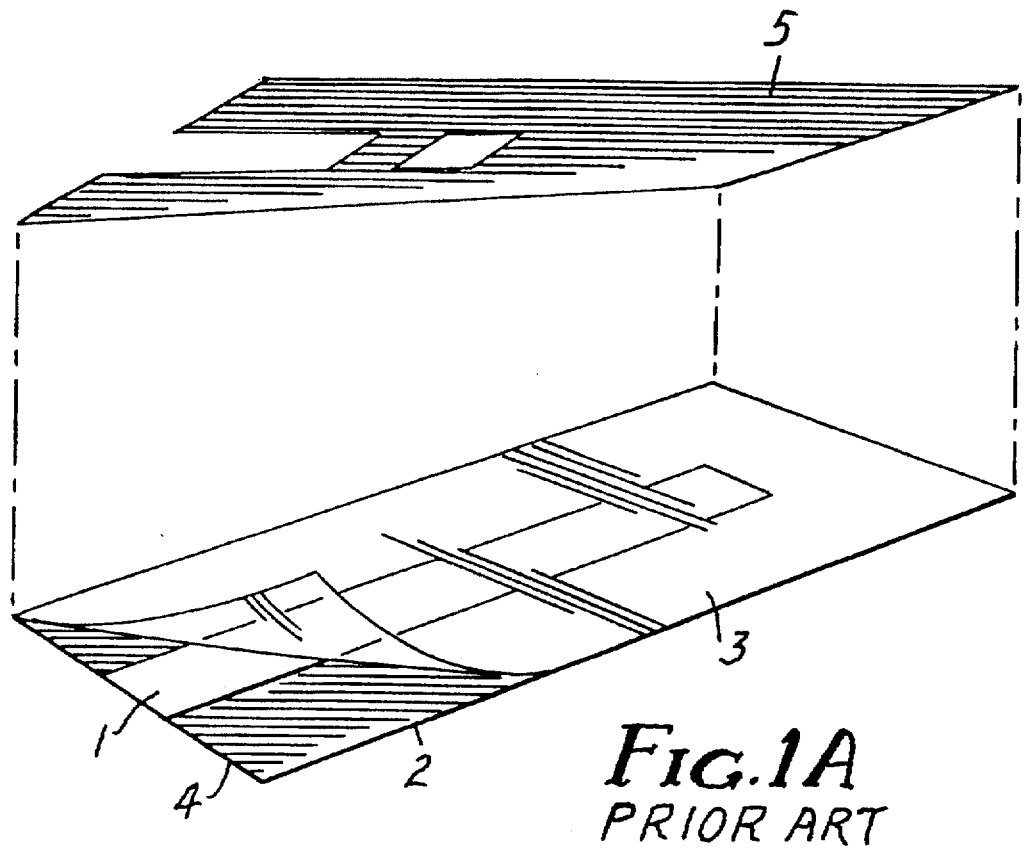
FIG. 1A is an exploded view of a prior art chemical indicator for ethylene oxide sterilization. (PRIOR ART)
Figure 1B:
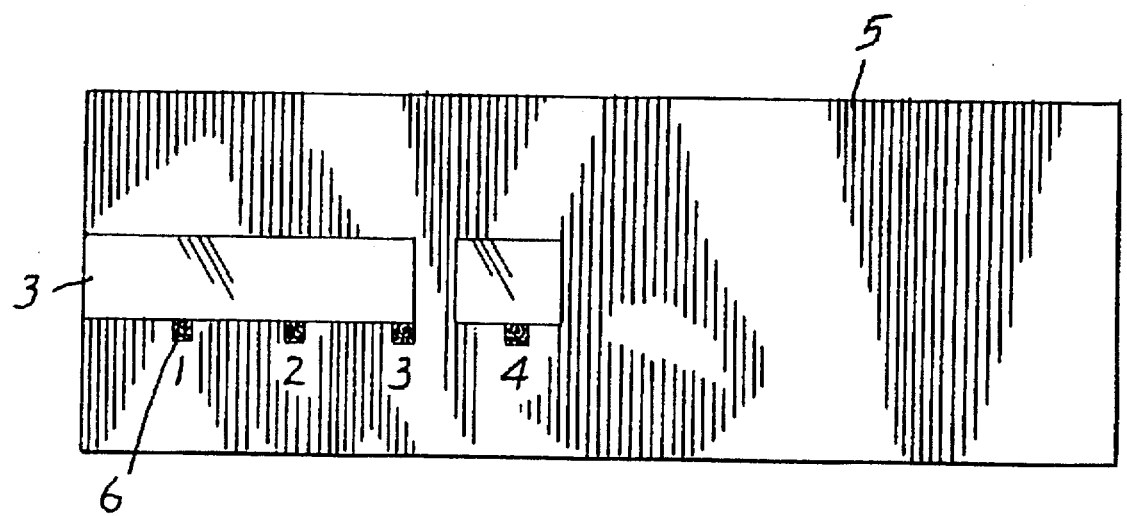
FIG. 1B is a plan view of the device of FIG. 1 showing label and scale. (PRIOR ART)

This invention relates to a test pack for determining the efficacy of an ETO sterilization process. In particular it relates to a test pack which utilizes the chemical type process monitor disclosed in U.S. Pat. No. 4,138,216, incorporated herein by reference. The device of the '216 patent is a wick type monitor which is responsive to ETO concentration, temperature and humidity. In order that the invention will be fully appreciated so much of the disclosure of the '216 patent as is necessary will be reproduced herein.

The monitor comprises a wick impregnated with a chemical compound which will react with ethylene oxide to form a basic product and a pH sensitive dye which will present a visual indication of the presence of the basic reaction product. Additionally, the wick may have incorporated therein a quantifier compound which determines the rate at which the response to the presence of ETO appears along the length of the wick. The color change proceeds along the wick in an analog fashion at a rate which for a given composition is a function of gas concentration, temperature and humidity.

The ETO sterilization process can be carried out utilizing either a diluted gas stream or 100% ETO. Generally the ETO is diluted to a concentration of about 12%, the diluent gas being preferably a chloro-fluoro hydrocarbon, e.g. Freon® 12.

The wick is enclosed in an envelope having one end open from which the wick protrudes. The envelope is constructed of an ethylene oxide impervious film, e.g. ethylene glycol/ terephthalic acid copolymer. Illustrative non-limiting examples of the chemical compounds reactive with ETO that may be used in preparing the chemical indicator include $MgCl_2$, $FeCl_2$, $ZnCl_2$ and the hydrates of these salts. A particularly preferred compound is the hydrate of magnesium chloride ($MgCl_2 \cdot 6H_2O$).

As used in the specification and claims the term "ethylene oxide responsive chemical compound" means chemical compounds which react with ETO to produce a basic reaction product of which the foregoing compounds are illustrative examples.

The material used for the wick is not critical. It need only be sufficiently absorbent to take up a solution containing the chemical compound, and not be attacked either by the constituents of the solution or ethylene oxide. Any fabric such as polyamides, polyesters, cotton etc., whether woven or non-woven is suitable. Of course the material selected must not be deleteriously affected by the basic reaction product or ethylene oxide. Paper is the preferred wick material.

The term "pH sensitive dye" as used in the specification and claims means a pH sensitive dye having at least one $PK_a$ value which is less than 8. Illustrative, non-limiting examples of the pH sensitive dyes which may be used in the practice of this invention are bromphenol blue, thymol blue and xylenol blue. The preferred pH sensitive dye is bromphenol blue. The pH sensitive dye useful in the practice of this invention have at least one $pK_a$ value which is less than 8; more preferably, less than 7.

The quantifier material is a compound which reacts preferentially with the basic reaction product thereby neutralizing it and preventing a color change of the pH sensitive dye. The preferred quantifiers are acids and acid salts of low volatility. Illustrative, non-limiting examples of such quantifiers are tartaric acid, oxalic acid, citric acid, sodium bisulfate, etc. The term "quantifier" as used in the specification and claims means a non-volatile acid compound having a $pK_a$ value of less than 6 which can react with the basic reaction product of ethylene oxide with the ethylene oxide responsive chemical compound.

Any material which is impervious to ethylene oxide may be used to form the envelope for enclosing the wick means. At least a part of the material must be transparent in order to display the wick. The preferred envelope materials are ethylene oxide impervious polymeric films, e.g. ethylene glycol/terephthalic acid copolymers. However, metal foils may be used as part of the envelope, e.g. aluminum foil or aluminum foil coated laminated with polyethylene or paper.

Illustrative non-limiting examples of ethylene oxide impervious films useful in preparing chemical type indicators are trifluoropolyethylene, polycarbonates, polyvinylidiene chloride and polyesters, in particular the ester of ethylene glycol and terephthalic acid (Mylar®).

In preparing the wick means the wick composition is impregnated with a solution of ethylene oxide responsive chemical compound, pH sensitive dye and a quantifier in a suitable solvent. The solvent should be a volatile compound such as $C_1$–$C_3$ alcohols. preferably the solvent is a water/ alcohol solution, preferably comprising about 40 to about 70% alcohol; more preferably about 50%.

Illustrative non-limiting examples of solvents useful in preparing the chemical type indicator are methanol, ethanol, methyl acetate, ethyl acetate, propanol, water and mixtures thereof. The preferred solvents are methanol, ethanol, water and mixtures thereof.

The chemical type indicator useful in the practice of this invention can be more readily appreciated by reference to drawings and in particular U.S. Pat. No. 4,138,216, incorporated herein by reference. Referring now to FIG. 1A, the wick, 1, is mounted on an adhesive coated backing, 2. A transparent, ethylene oxide impervious cover strip, 3, is adhered to the backing strip, 2, completely enclosing the wick except for one open end, 4. When the cover strip, 3, is adhered to the backing strip, 2, the wick, 1, is exposed only along the open end, 4.

In another embodiment the backing strip is adhered to the cover strip by heat sealing. As shown in FIG. 15, for convenience of use a label, 5, may be adhered to the cover strip so that a scale, 6, may be imprinted thereon.

In practicing the instant invention a commercially available chemical type ethylene oxide indicator manufactured and sold by 3M under its trademark THERMALOG® G, was utilized. Rather than a scale, the device has two windows in tandem exposing the wick to view. A first window is marked "UNSAFE." The following window exposing the wick is labeled "SAFE." The sterilization process is deemed to have been effectively completed when a color change appears in the second window. The process is generally timed so that the entire second window, or at least a substantial pert of it is filled with an observed color change. In order for the indicator to display an integrated time, temperature, humidity, ETO exposure sufficient for sterilization, the wick color must change from yellow to blue completely filling the first window, with the blue coloration indicating reaction of the ETO and components of the wick, and moving into the second window. The particular device described is designed with a 90 minute time frame to indicate sterilization when it is wrapped in a packaging of material to be sterilized. The term "chemical type indicator" as used in the specification and claims means the indicator of the type disclosed in U.S. Pat. No. 4,138,216, and further described herein. This device which is commercially available has a nominal length of 4 inches, and a width of 0.750 inches. The wick means is about 3.875 inches in length. The backing strip is an aluminum foil/paper laminate. When tested at a relative humidity of 50% at 130° F., and a gas concentration of 600 mg/L, (Freon 12/12% ETO) the device will reach the "SAFE" window within 90 min.

Figure 2:
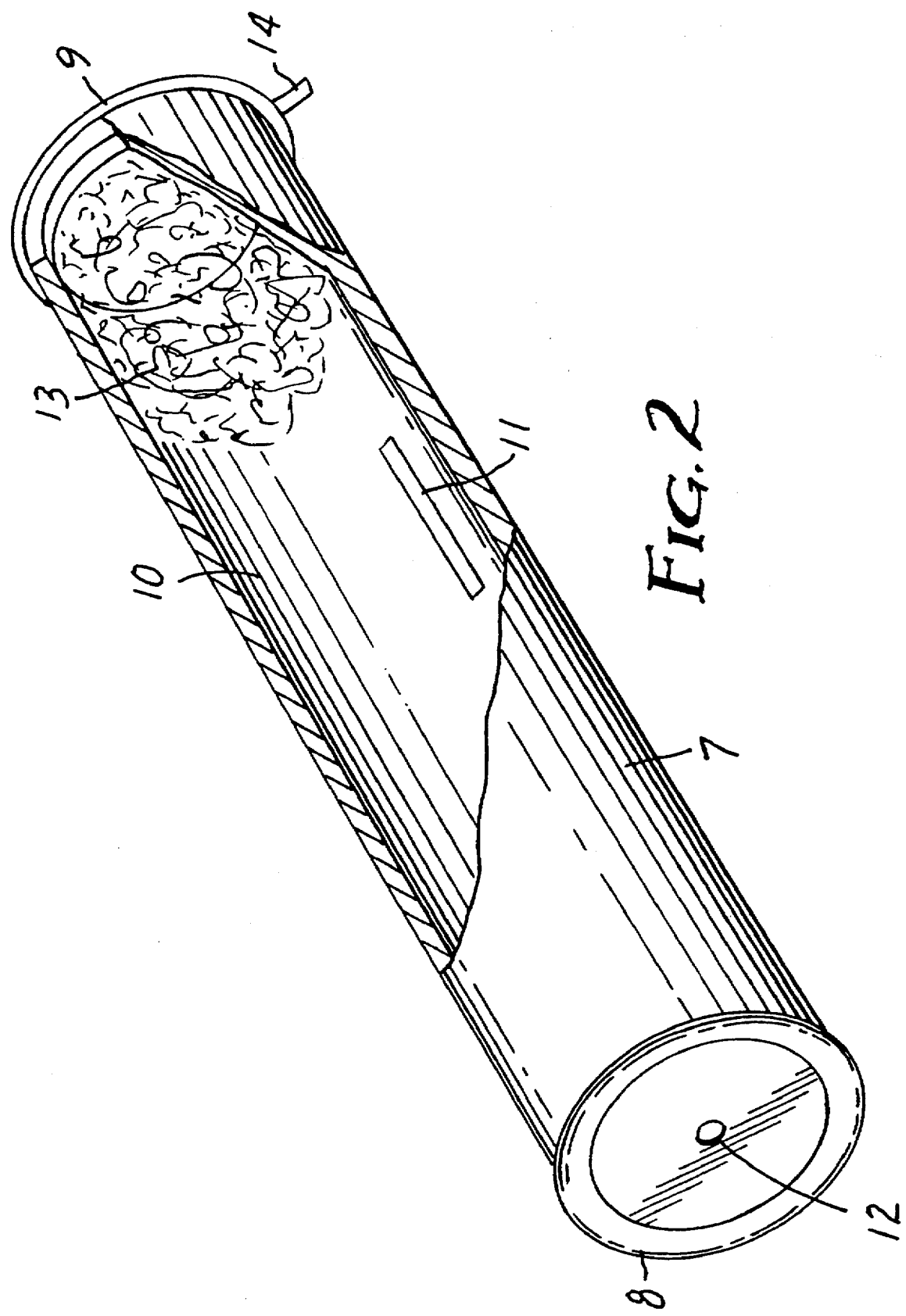
FIG. 2 is a cut away view of the test pack of this invention.

In the practice of the invention rather than wrapping the chemical type indicator in a packaging, it is placed in the test pack of this invention. Referring now to FIG. 2, a tube, 7, made of fiber board is enclosed by end caps, 8 and 9, thereby defining a test chamber, 10. A chemical type indicator, 11, is placed in the chamber. End cap, 8, has an opening, 12, in it to permit the egress of ETO into the test chamber, 10, activating the chemical type indicator, 11. The opening, 12, can be about 2.5 mm to about 3.5 mm in diameter; typically, 3 mm. A fiber ball, 13, is placed in the test chamber at the end remote from the opening, 12.

The fiber ball, 13, can be about 250 mg. to about 360 mg. in weight, and have a bulk density of about 13.5 mg/cc to about 43 mg/cc. Typically, the weight of the fiber ball can be about 290 mg. to about 340 mg., e.g. 300 mg. Typically, the bulk density of the fiber ball can be about 24.5 mg/cc to about 35 mg/cc, e.g. 30 mg/cc. The fiber ball should be made of a material which can absorb both moisture and ethylene oxide. Illustrative non-limiting examples of materials suitable for use in the fiber ball are rayon and cotton. It will be appreciated by those skilled in the art having access to this disclosure that use of the term "ball" in the context of this invention does limit the shape to a strictly spherical one, since the fiber "ball" will be distorted when it is inserted into the fiber board tube.

The fiber board tube used in the examples described below had a length of about six inches, an outer diameter of about 1.375 inches and an inner diameter of about 0.875 inches. The length of the fiber board tube can vary by about 0.5 of an inch and the diameters may vary in size by about 0.125 of an inch. A typical tube construction utilizes Convolute DURO paper with dextrine adhesive to form the fiber board tube.

The end caps, 8 and 9, can be made of a polymeric material or metal. Where a polymeric material is used it should either be ethylene oxide impervious or of sufficient thickness so that the diffusion of ETO through the end cap during the test period is negligible as compared to the volume of ETO entering the chamber.

The end cap, 9, can optionally be provided with a tab, 14, which is used to remove the end cap in order to retrieve the chemical type indicator, 11. It will be appreciated by those skilled in the art having access to this disclosure that the tab, 14, can be placed on either cap.

The term "test pack" as used in the specification and claims with respect to the device of this invention means the fiber tube with its end caps in place, the fiber ball located as heretofore described, and a chemical type indicator placed within the test chamber. The term "test chamber" as used in the specification and claims means the space defined within the fiber board tube with the end caps in place.

Based on a 90 minute sterilization cycle required for sterilization, tests were preformed on various modifications of the invention to establish criticality of the embodiments claimed. The criterium for proper operation of the chemical type indicator is that it must display a color front in the second window at ninety minutes, thereby evidencing successful sterilization. Additionally, no color front should be visible in the second window at an exposure time to ETO of less than 60 minutes. The test packs were placed in pouches prior to testing. In one embodiment the test pack is enclosed in a pouch having a first face comprising a polymeric film, e.g. polyester/propylene laminate heat sealed to an opposing second face of paper, typically bleached surgical kraft paper, which permits the access of ETO to the test pack. The paper presently being used in the practice of this invention has a porosity of 10–35 seconds per 100 cc under a pressure of 20 oz. The pouch has three sealed edges and is adapted to be sealable along the fourth edge. The pouch can be sealed by use of an adhesive coated flap or by applying adhesive to the inner surface of one face and covering the adhesive with a release paper until sealing is desired. It will be appreciated that the size of the pouch is not critical. A pouch of about 13⅜ inches in length and width of 5 inches is typically used. The sterilization cycle includes a 24 hour aeration cycle at room temperature in order to remove unreacted ethylene oxide. The aeration step is required so that goods which have undergone ETO sterilization will be free of residual ETO. At the conclusion of the sterilization process the test pack is removed from the pouch, opened, and the indicator removed and read to determine the efficacy of the process.

In the following examples all of the test packs had labels wrapped around the tube made of Fasson™ label stock. Changing the label stock did not have any significant effect on performance. All test were run with the test packs enclosed in a pouch. It was constructed of a clear, laminate of 1.5 mil polypropylene and 0.48 mil of polyester, with an opposing paper face as described above. The use of the combination of a label and the pouch will change the test results from those obtained with a naked tube and no pouch. Those skilled in the art can adjust such parameters as the size of the ETO inlet perforation or thickness of the tube without undue experimentation to achieve test results consistent with the manner in which the tests are performed. What variables are used will depend on the run time to "SAFE" which is desired. The examples which follow used a 3 mm ETC entry hole.

The chemical indicator utilized in the practice of this invention is placed in the test chamber with the open edge of the indicator facing the ETO access hole.

EXAMPLE I

Chemical indicators were placed in individual tubes with the end caps in place but no fiber ball in the test chamber. Two sets of three samples were exposed to an ETC gas stream containing 12% ETC for 30 minutes and 60 minutes respectively. The temperature was 56° C. with a humidity of 60%. The samples run for 30 minutes displayed a color front in the first window only, indicating an unsafe condition. Of the samples run for 60 minutes all three displayed a color front in the second window evidencing sterilization even though the cycle time was too short to meet the predetermined test time criterium to ensure sterilization.

Two groups of three control samples were run at the same time for 30 and 60 minutes. These samples were fully exposed in the autoclave and both sets reach the "SAFE" window as would be expected.

EXAMPLE II

Example I was repeated with the modification that a fiber ball (Rayon{ }) was placed in the test chamber adjacent to the cap containing the ETC entry hole. At 30 minutes the samples indicated an unsafe (not sterilized) condition. At ninety minutes the samples still failed to show a safe condition notwithstanding the fact that the sterilization cycle was sufficient to ensure sterilization.

The obstruction at the end with the hole created by the presence of the Rayon® fiber ball resulted in a negative result. The fiber ball in this position is equivalent to the tortuous paths of the prior art devices

EXAMPLE III

Example I was repeated except that a rayon fiber ball was placed at the end of the test chamber remote from the opening in the end cap. Both the 30 minute and 60 minute test showed an unsafe condition.

EXAMPLE IV

Sixteen samples were prepared with the rayon ball placed at the end of the test chamber remote from the entry hole. After ninety minutes exposure all samples displayed a safe, sterilized, condition.

The foregoing Examples demonstrate that the position of the fiber ball is critical. It must be located at the end of the test chamber which is remote from the ETO entry hole. Surprisingly, unlike prior art devices the fiber ball cannot be located in a position which results in the equivalent of the prior art tortuous path or packing.

What is claimed is:

1. A test pack for evaluating an ethylene oxide sterilization process, comprising:
   (a) an open ended fiber board tubular member having first and second end;
   (b) a first end cap enclosing the first end of said tubular member,
   (c) a second end cap enclosing the second end of said tubular member,
   said first and second end caps defining a test chamber within the tubular member, said first end cap having an opening to permit the entry of ethylene oxide into the test chamber; said second end cap being closed to substantially restrict access of ethylene oxide into said test chamber through said second end cap;
   (d) a fiber ball located in the test chamber; and
   (e) a chemical type sterilization indicator located within the test chamber and spaced from said first end cap;
   said fiber ball being located in said test chamber substantially adjacent said chemical indicator and said second end cap, said fiber ball being spaced from said first end cap, wherein the space between said first end cap and at least a portion of said chemical indicator is substantially free of any structures capable of substantially impeding the flow of ethylene oxide.

2. The test pack according to claim 1 wherein the fiber ball comprises rayon fiber or cotton fiber.

3. The test pack according to claim 1 wherein the fiber ball comprises rayon fiber.

4. The test pack according to claim 1 wherein the first and second end caps are made of metal or a polymeric material.

5. The test pack according to claim 1 wherein the chemical type ethylene oxide sterilization indicator utilizes a paper wick.

6. The test pack according to claim 1 enclosed within a pouch having at least one face which is permeable to ethylene oxide.

7. The test pack according to claim 6 wherein the ethylene oxide permeable face is paper.

8. The test pack according to claim 6 wherein the pouch comprises a first face impermeable to ethylene oxide consisting of ethylene glycol-terephthalic acid ester/polypropylene laminate, and an opposing paper trace, the pouch being sealed along three edges, and having a sealable forth edge through which the test pack can be inserted, and subsequently sealed.

9. The pouch according to claim 8 wherein the paper face has a message imprinted thereon which is readable through the ethylene oxide impermeable face.

* * * * *